(12) United States Patent
Wieters et al.

(10) Patent No.: US 11,589,735 B2
(45) Date of Patent: Feb. 28, 2023

(54) OPTICAL CONNECTING DEVICE FOR A SURGICAL INSTRUMENT

(71) Applicant: OLYMPUS WINTER & IBE GMBH, Hamburg (DE)

(72) Inventors: Martin Wieters, Barsbuettel (DE); Alexander Krueger, Seevetal (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 141 days.

(21) Appl. No.: 17/186,735

(22) Filed: Feb. 26, 2021

(65) Prior Publication Data
US 2021/0267437 A1    Sep. 2, 2021

(30) Foreign Application Priority Data
Feb. 27, 2020   (DE) .......................... 102020105125.5

(51) Int. Cl.
*A61B 1/00*    (2006.01)

(52) U.S. Cl.
CPC ........ *A61B 1/00124* (2013.01); *A61B 1/0014* (2013.01); *A61B 1/00117* (2013.01); *A61B 1/00126* (2013.01); *A61B 1/00165* (2013.01)

(58) Field of Classification Search
CPC ............ A61B 1/00117; A61B 1/00124; A61B 1/00126; A61B 1/0014; A61B 1/00165
See application file for complete search history.

(56) References Cited

U.S. PATENT DOCUMENTS

| | | | | |
|---|---|---|---|---|
| 4,414,608 A | * | 11/1983 | Furihata | A61B 1/00117 396/17 |
| 4,706,653 A | * | 11/1987 | Yamamoto | A61B 1/00096 600/127 |
| 2008/0306470 A1 | | 12/2008 | Friedman | |
| 2019/0038120 A1 | | 2/2019 | MacLean et al. | |

* cited by examiner

*Primary Examiner* — Aaron B Fairchild
(74) *Attorney, Agent, or Firm* — Scully, Scott, Murphy & Presser, P.C.

(57) ABSTRACT

An optical connecting device for a surgical instrument including a coupling for connecting first and second optical fiber bundles. The coupling including: a tubular sleeve having an outer surface defining an internal space for receiving an end of the first optical fiber bundle in the internal space of the tubular sleeve; a clamp movably disposed on the outer surface of the tubular sleeve, the clamp having one or more of a first convexity and a first concavity; and a union having one or more of a second convexity and a second concavity. The clamp has a continuous longitudinal opening along its longitudinal extension and on its outer side such that the clamp can be elastically deformed in a radial direction, and the clamp is configured to elastically deform such that one or more of the first convexity and the first concavity engages with one or more of the second convexity and the second concavity of the union.

12 Claims, 1 Drawing Sheet

OPTICAL CONNECTING DEVICE FOR A SURGICAL INSTRUMENT

CROSS-REFERENCE TO RELATED APPLICATION

The present application is based upon and claims the benefit to DE 10 2020 105 125.5 filed on Feb. 27, 2020, the entire contents of which are incorporated herein by reference.

BACKGROUND

Field

The present disclosure generally relates to an optical connecting device, and more particularly to a screwable optical connecting device, for a surgical instrument, such as for an endoscope.

Prior Art

It is known that, in the case of endoscopes, light is transferred from one fiber optic bundle into a second fiber optic bundle, preferably in the handle. During the coupling of the fiber optic bundles, it is provided that the distances between the light outlet faces and the light inlet faces of the ends of the fiber optic bundles, which are located opposite one another, are kept small. In particular, the fiber optic bundles or respectively the ends thereof are fixed using screws.

SUMMARY

An object consists of guaranteeing a secure positioning and/or fixing of fiber optic bundles during a coupling of two fiber optic bundles in a simple manner.

Such object can be solved by an optical connecting device, such as a screwable optical connecting device, for a surgical instrument, such as an endoscope, having a coupling for an optical fiber bundle, wherein the coupling has a sleeve having an internal space for receiving one end of the optical fiber bundle in the internal space of the sleeve and a sleeve-like clamp, wherein the sleeve for the fiber bundle is enclosed by the clamp, wherein the sleeve-like clamp has a continuous longitudinal opening along its longitudinal extension and on its outer side, such as at one end, is configured with a detent for arrangement in a latching connecting link, such as a latching connecting link of a union nut, and/or with a latching groove for receiving a latching projection, such as a latching projection of a union nut.

A sleeve-like clamp can be used to fix the sleeve for the optical fiber bundle, wherein in order to position the sleeve-like clamp or respectively to receive the sleeve-like clamp, e.g., in a union nut, the sleeve-like clamp can be configured with a latching groove, into which a latching projection, e.g., a union nut, is brought into engagement. In order to arrange the sleeve-like clamp on the sleeve for the optical fiber bundle, the sleeve-like clamp can be pushed laterally over the sleeve for the fiber bundle and is compressed in order to be arranged in a union nut such that the union nut is guided via the (compressed) clamp, as a result of which at least one end of the clamp is received by the union nut and, as a result, the clamp is positioned inside the union nut by the detent and/or the latching groove.

The sleeve-like clamp can have a continuous longitudinal opening along its longitudinal extension, i.e., the clamp can have a hollow cylinder which is open at the longitudinal side. In the axial direction, the clamp can have, in a configuration, a hooking portion having a latching groove and/or a detent which is introduced, for example, into a latching connecting link or the union nut, or which interacts with a latching projection of the union nut. The latching connecting link of the union nut can be configured in the form of a groove or in the shape of a "U".

Moreover, the sleeve-like clamp can have a guiding-out portion, wherein the guiding-out portion serves to guide the clamp out of the union nut. The clamp additionally can have a handling portion which serves to grasp or respectively handle and to compress the clamp.

Due to the elongated or respectively longitudinally extended embodiment of the sleeve-like clamp, the functional portions can be arranged axially, i.e., not radially, as a result of which the requirement for radial installation space for the clamp is, for example, reduced.

Moreover, it is provided in a configuration that the longitudinal opening of the clamp can extend parallel to the longitudinal axis of the clamp.

An end-sided detent and/or an end-sided latching groove can be arranged at one end of the clamp, which can be arranged or received in the union nut, wherein a portion of the clamp facing away from the detent and/or from the latching groove projects out of the union nut.

According to a further aspect, it is provided in the case of the optical connecting device that the detent and/or the latching groove of the clamp in the peripheral direction of the clamp can be configured circumferentially in the peripheral direction. Furthermore, the sleeve for the fiber bundle can have at least one end-sided collar, such as two end-sided collars. In the case of the optical connecting device that an end-sided collar can be arranged in the union nut, configuring the connecting device, wherein the clamp, which is positioned at the end of the union nut, serves or respectively is configured as a stop for the received sleeve, as a result of which the end-sided collar of the sleeve rests with one end, which is arranged in the union nut, on the clamp.

To this end one or the end-sided collar of the sleeve can have an outside diameter which is larger than the inside diameter of the clamp. As a result, a secure positioning of the end-sided collar with the sleeve is achieved on the clamp.

One or the end-sided collar of the sleeve can be received in a union nut.

A latching projection of the union nut can be arranged in the latching groove of the clamp. In a further configuration, a detent of the clamp can be arranged in or hooked into a latching connecting link, such as groove-shaped latching connecting link, of the union nut. As a result, a secure arrangement of the sleeve-like clamp in or respectively on the union nut is achieved.

In addition, the union nut can have, on its end side, an inwardly projecting latching projection which can be circumferential on the inner side, wherein the latching projection of the union nut interacts, such as being complementary in form and/or function, with the detent and/or with the latching groove of the clamp.

The sleeve-like clamp can be produced from plastic, such as from polyether ether ketone (PEEK).

The sleeve can have, at its ends, two collars, wherein the outside diameters of the collars can differ at both ends, and wherein the collar having the larger outside diameter can be arranged in the region of the end of the fiber bundle. The end-sided collar having the larger outside diameter can be received in the union nut, configuring the connecting device. The second end-sided collar having the smaller diameter can be positioned outside the union nut, wherein, the outside diameter of the end-sided collar can be larger than the inside diameter of the sleeve-like clamp. The clamp can be arranged between the collars of the sleeve.

The union nut can have a receiving space for a sleeve of a second fiber bundle. An internal space, in which one end of a fiber bundle is arranged, can be provided in the sleeve. As a result, a secure positioning of the second fiber bundle or respectively the end thereof in the union nut is achieved, wherein the end of the second fiber bundle can be arranged opposite the end of the fiber bundle which is received in the sleeve for the first fiber bundle.

Moreover, the union nut can have latching means for secure positioning of the sleeve of the second fiber bundle in the receiving space for the sleeve of the second fiber bundle.

The object can be additionally solved by a surgical instrument, such as an endoscope, having an optical connecting device, as described above.

To avoid repetitions, reference is expressly made to the above embodiments.

Further features will become evident from the description of embodiments, together with the claims and the appended drawings. Embodiments can fulfill individual features or a combination of multiple features.

BRIEF DESCRIPTION OF THE DRAWINGS

The embodiments will be described below without limiting the general concept of the invention by means of exemplary embodiments with reference to the drawings, wherein reference is expressly made to the drawings regarding all of the details which are not explained in greater detail in the text, wherein.

DETAILED DESCRIPTION

Figure 1:
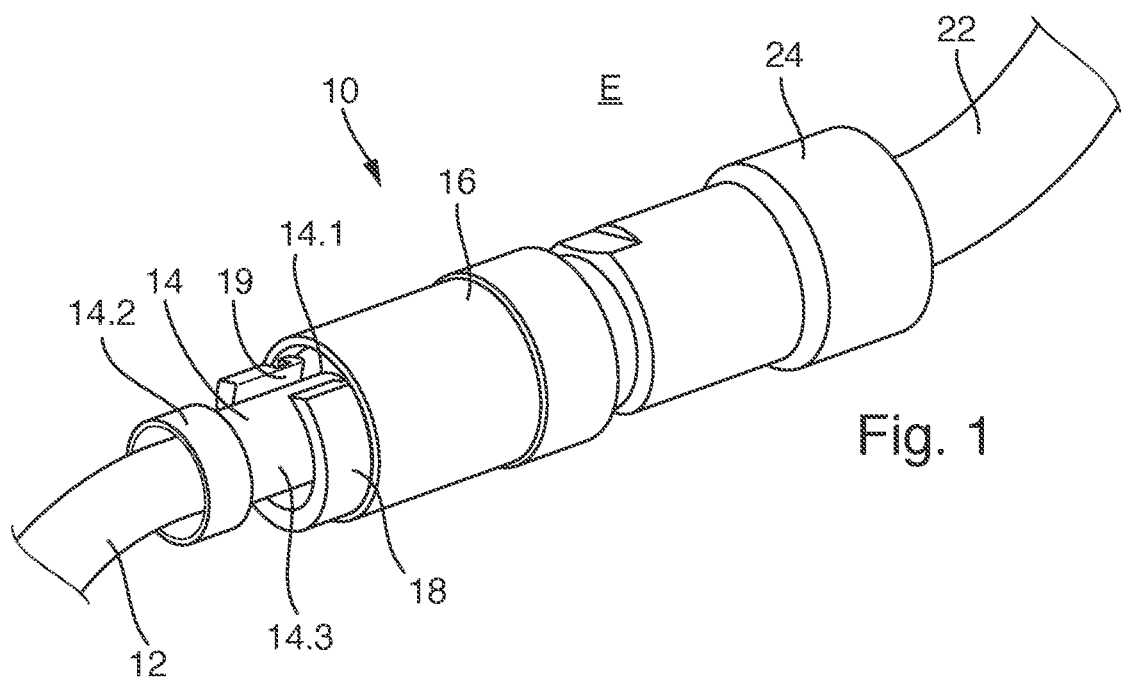
FIG. 1 illustrates a perspective view of a connecting device for two optical fiber bundles in the detail.

In the drawings, the same or similar elements and/or parts are, in each case, provided with the same reference numerals such that they are not introduced again in each case.

Figure 2:
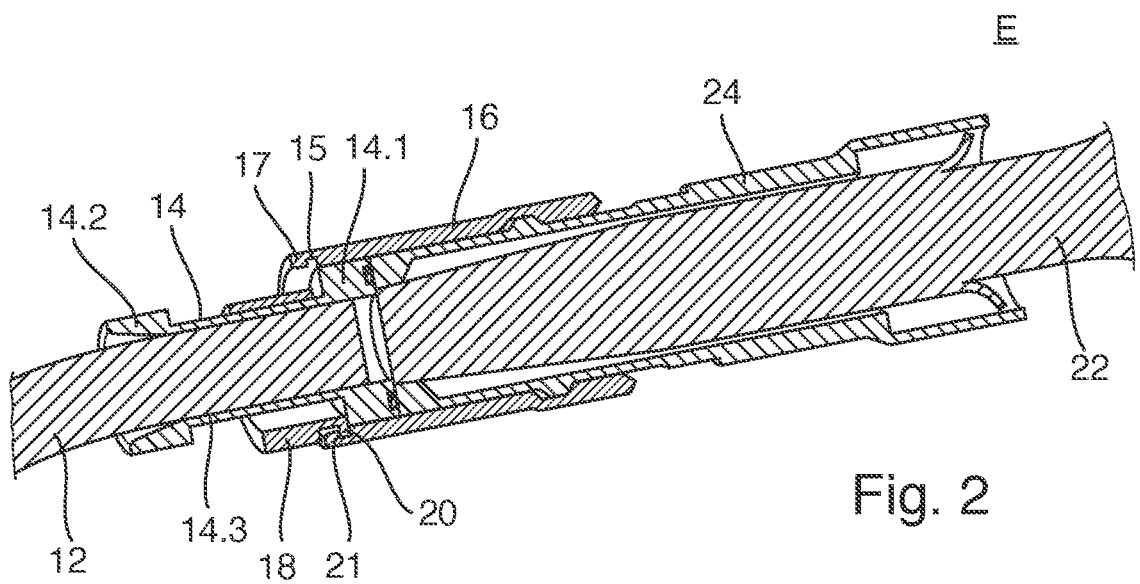
FIG. 2 illustrates a cross-section through the connecting device.

In FIG. 1, a perspective view of a connecting device 10 for two fiber optic bundles 12, 22 is schematically represented. In FIG. 2, a cross-section through the connecting device 10 is shown. The connecting device 10 is an integral part of an endoscope E (which is not represented here).

Light from, for example, the fiber optic bundle 12 is coupled by means of the fiber optic bundles 12, 22 into the second fiber optic bundle 22, in order to conduct the light inside an endoscope shaft to the distal tip of the endoscope E.

The (first) fiber optic bundle 12 has, at its end, a sleeve 14, wherein the end of the fiber optic bundle 12 is received in a cylindrically formed hollow space of the sleeve 14. The sleeve 14 has a collar 14.1, 14.2 at each of its ends, between which a tubular element 14.3 is configured. The collar 14.1 is configured with a tapering inner contour. The outside diameter of the collars 14.1, 14.2 is larger than the outside diameter of the tubular element 14.3.

The connecting device 10 additionally has a union nut 16, in which the collar 14.1 of the sleeve 14 is received. The union nut 16 features an internal thread which interacts with an external thread on the outer side of the collar 14.1 such that the sleeve 14 is securely positioned inside the union nut 16 and, therefore, the end of the end of the fiber optic bundle 12 received by the sleeve 14 is securely positioned.

The connecting device 10 has a clamping body 18 which is configured in a sleeve-like manner. The clamping body 18 has a longitudinal extension, wherein a longitudinal opening 19 is configured along the longitudinal extension on one side of the clamping body 18 such that the clamping body 18 is or will be pushed laterally over the tubular element 14.3 of the sleeve 14, as a result of which the clamping body 18 surrounds the tubular element 14.3.

At the end of the clamping body 18 facing the collar 14.1 of the sleeve 14, a latching groove 21 is configured on the outer side of the clamping body 18. Moreover, a detent 20 is configured at the end of the clamping body 18.

The clamping body 18 can be configured from a material having an elastic deformation characteristic, such as polyether ether ketone (PEEK), such that the clamping body 18 can be deformed inwardly in the radial direction with the application of a compressing force. In such state, the clamping body 18 is moved longitudinally so that the latching groove 21 and detent 20 corresponds to the latching projection 17 and groove 15 in the longitudinal direction. When a compressing force on the clamping body is then released, the clamping body expands radially and the latching groove 21 and detent 20 engage with the latching projection 17 and groove 15. In addition, the sleeve 24 and the union nut 16 as well as the sleeve 24 are preferably produced from metal, in particular stainless steel.

The union nut 16 has, at its end facing the sleeve 14, a circumferential groove 15, as a result of which the end of the union nut 16 has a latching projection 17. The latching projection 17 of the union nut 16 is brought into engagement with the latching groove 18 of the clamping body 18, wherein, in addition, the detent 20 of the clamping body 18 engages in the circumferential groove 15 of the union nut 16.

The second fiber optic bundle 22 is enclosed at its end, which is arranged opposite the end of the first fiber optic bundle 12, by a sleeve 24, the front end of which is received in the union nut 16. The front end of the sleeve 24 is provided with an external screw thread which engages in an internal thread of the union nut 16, as a result of which the sleeve 24 is securely positioned in the union nut 16.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

10 Connecting device
12 Fiber optic bundle
14 Sleeve
14.1, 14.2 Collar
14.3 Tubular element
15 Groove
17 Latching projection
18 Clamping body
19 Longitudinal opening
20 Detent
21 Latching groove
22 Fiber optic bundle
24 Sleeve
E Endoscope

What is claimed is:

1. An optical connecting device for a surgical instrument, the optical connecting device comprising:
   a coupling for connecting first and second optical fiber bundles, the coupling comprising:
      a tubular sleeve having an outer surface defining an internal space for receiving an end of the first optical fiber bundle in the internal space of the tubular sleeve;
      a clamp movably disposed on the outer surface of the tubular sleeve, the clamp having one or both of a first convexity and a first concavity; and
      a union having one or both of a second convexity and a second concavity;
   wherein the clamp has a continuous longitudinal opening along a longitudinal direction and on an outer side such that the clamp can be elastically deformed in a radial direction, and
   the clamp is configured to elastically deform such that one or both of the first convexity and the first concavity engages with one or both of the second convexity and the second concavity of the union.

2. The optical connecting device according to claim 1, wherein the longitudinal opening of the clamp extends parallel to a longitudinal axis of the clamp.

3. The optical connecting device according to claim 1, wherein one or both of the first concavity and the first convexity are configured circumferentially on an exterior surface of the sleeve-like clamp.

4. The optical connecting device according to claim 1, wherein the tubular sleeve has a collar on at least one of first and second ends, the collar having a greater diameter than the outer surface of the tubular sleeve.

5. The optical connecting device according to claim 4, wherein the collar is a first collar disposed on the first end, the tubular sleeve further comprising a second a collar disposed on the second end.

6. The optical connecting device according to claim 5, wherein the first collar at the first end has a different outer diameter than an outer diameter of the second collar at the second end.

7. The optical connecting device according to claim 6, where the first collar at the first end corresponds to the end of the first fiber bundle, the first collar having a greater outer diameter than the outer diameter of the second collar.

8. The optical connecting device according to claim 1, wherein the sleeve-like clamp is formed from plastic.

9. The optical connecting device according to claim 8, wherein the plastic is polyether ether ketone (PEEK).

10. The optical connecting device according to claim 1, wherein the union has a receiving space for a sleeve containing the second fiber bundle.

11. A surgical instrument comprising the optical connecting device according to claim 1.

12. An endoscope comprising the optical connecting device according to claim 1.

* * * * *